(12) United States Patent
Puolakanaho

(10) Patent No.: US 9,721,141 B2
(45) Date of Patent: Aug. 1, 2017

(54) WRIST-WORN APPARATUS CONTROL WITH FINGERPRINT DATA

(71) Applicant: Polar Electro Oy, Kempele (FI)

(72) Inventor: Pertti Puolakanaho, Kiviniemi (FI)

(73) Assignee: POLAR ELECTRO OY, Kempele (FI)

(*) Notice: Subject to any disclaimer, the term of this patent is extended or adjusted under 35 U.S.C. 154(b) by 0 days.

(21) Appl. No.: 14/528,632

(22) Filed: Oct. 30, 2014

(65) Prior Publication Data
US 2016/0125219 A1 May 5, 2016

(51) Int. Cl.
| | |
|---|---|
| G06K 9/00 | (2006.01) |
| G06K 9/62 | (2006.01) |
| G06F 17/30 | (2006.01) |
| A61B 5/00 | (2006.01) |
| A61B 5/11 | (2006.01) |
| A61B 5/024 | (2006.01) |

(52) U.S. Cl.
CPC ........ G06K 9/00033 (2013.01); A61B 5/1118 (2013.01); A61B 5/7475 (2013.01); G06F 17/30247 (2013.01); G06K 9/6202 (2013.01); A61B 5/02438 (2013.01)

(58) Field of Classification Search
CPC .. G06K 9/66; G06K 9/32; G06K 9/46; G06K 9/62; G06K 9/6202; G06K 9/00033; H04N 7/01; A61B 5/7475; A61B 5/1118; A61B 5/02438; G06F 17/30247
See application file for complete search history.

(56) References Cited

U.S. PATENT DOCUMENTS

| | | | | |
|---|---|---|---|---|
| 5,735,800 | A * | 4/1998 | Yasukawa | A61B 5/02438 600/310 |
| 6,675,041 | B2 * | 1/2004 | Dickinson | A61B 5/02438 128/921 |
| 6,832,109 | B2 * | 12/2004 | Nissila | A61B 5/0245 600/509 |
| 6,984,207 | B1 * | 1/2006 | Sullivan | A61B 5/0002 600/300 |
| 7,198,607 | B2 * | 4/2007 | Jamsen | A61B 5/6831 600/300 |
| 7,327,859 | B1 * | 2/2008 | Chau | G06K 9/00046 382/116 |

(Continued)

OTHER PUBLICATIONS

US 9,607,205, 03/2017, Setterberg (withdrawn)*
(Continued)

*Primary Examiner* — Chan Park
*Assistant Examiner* — Mia M Thomas
(74) *Attorney, Agent, or Firm* — Hoffman & Baron, LLP

(57) ABSTRACT

A wrist-worn apparatus control with fingerprint data includes a physical activity-related measurement sensor interface, a fingerprint sensor, one or more processors, and one or more memories including computer program code. The one or more memories and the computer program code are configured to, with the one or more processors, cause the apparatus at least to receive fingerprint data from a user with the fingerprint sensor, identify the fingerprint data as matching with one finger of the user on the basis of a comparison between the fingerprint data and reference data of a plurality of fingers of the user stored in the memory, and select a function of a physical activity-related measurement on the basis of the identified finger.

26 Claims, 11 Drawing Sheets

(56) References Cited

U.S. PATENT DOCUMENTS

| | | | |
|---|---|---|---|
| 7,334,472 B2* | 2/2008 | Seo | A61B 5/222 73/379.01 |
| 7,771,320 B2* | 8/2010 | Riley | A63B 24/0006 434/238 |
| 8,717,254 B1* | 5/2014 | Nave | G09G 3/003 345/7 |
| 8,945,017 B2* | 2/2015 | Venkatraman | A61B 5/721 600/500 |
| 8,948,832 B2* | 2/2015 | Hong | A61B 5/02427 600/301 |
| 8,954,135 B2* | 2/2015 | Yuen | A61B 5/0002 600/407 |
| 2002/0007249 A1* | 1/2002 | Cranley | A61B 5/00 702/24 |
| 2002/0009972 A1* | 1/2002 | Amento | G06F 3/017 455/66.1 |
| 2002/0013717 A1* | 1/2002 | Ando | A61B 5/0002 705/4 |
| 2003/0046228 A1* | 3/2003 | Berney | G06F 21/32 705/41 |
| 2004/0263358 A1* | 12/2004 | Madsen | G06F 3/033 341/20 |
| 2005/0060001 A1* | 3/2005 | Singhal | A61N 1/36135 607/19 |
| 2006/0256074 A1* | 11/2006 | Krum | G06F 1/1626 345/156 |
| 2007/0100244 A1* | 5/2007 | Lin | A61B 5/02438 600/503 |
| 2007/0116329 A1* | 5/2007 | Tsubata | A61B 5/02438 382/115 |
| 2007/0271065 A1* | 11/2007 | Gupta | A43B 3/0005 702/160 |
| 2008/0048972 A1* | 2/2008 | Kakarala | G06F 3/042 345/156 |
| 2008/0266118 A1* | 10/2008 | Pierson | A61B 5/0205 340/573.6 |
| 2009/0082066 A1* | 3/2009 | Katz | G06F 1/3203 455/566 |
| 2010/0076331 A1* | 3/2010 | Chan | A61B 5/0006 600/522 |
| 2010/0156676 A1* | 6/2010 | Mooring | G06F 3/017 341/20 |
| 2010/0185252 A1* | 7/2010 | Bjorling | A61B 5/0031 607/19 |
| 2010/0201639 A1* | 8/2010 | Huang | G06F 3/0428 345/173 |
| 2010/0228724 A1* | 9/2010 | Petri | G06F 17/30489 707/722 |
| 2011/0027766 A1* | 2/2011 | Yoo | A61H 5/00 434/262 |
| 2011/0066004 A1* | 3/2011 | Sullivan | A61B 5/0002 600/300 |
| 2011/0081037 A1* | 4/2011 | Oh | A61B 5/02438 381/380 |
| 2011/0138285 A1* | 6/2011 | Kuo | G06F 3/017 715/727 |
| 2011/0199470 A1* | 8/2011 | Moller | G06F 1/1686 348/61 |
| 2011/0210931 A1* | 9/2011 | Shai | G06F 3/014 345/173 |
| 2011/0270055 A1 | 11/2011 | Kraemer et al. | |
| 2011/0300829 A1 | 12/2011 | Nurmi et al. | |
| 2012/0239173 A1* | 9/2012 | Laikari | A61B 5/1112 700/91 |
| 2014/0028546 A1* | 1/2014 | Jeon | G06F 3/014 345/156 |
| 2014/0028914 A1* | 1/2014 | Polak | H04N 5/04 348/515 |
| 2014/0055352 A1* | 2/2014 | Davis | G06F 3/017 345/156 |
| 2014/0085269 A1* | 3/2014 | Armstrong-Muntner | G06F 3/03545 345/179 |
| 2014/0107493 A1* | 4/2014 | Yuen | H04W 4/027 600/473 |
| 2014/0135631 A1* | 5/2014 | Brumback | A61B 5/02438 600/479 |
| 2014/0139486 A1 | 5/2014 | Mistry et al. | |
| 2014/0239065 A1 | 8/2014 | Zhou et al. | |
| 2015/0106868 A1* | 4/2015 | Lo | G06F 21/32 726/1 |
| 2015/0269409 A1* | 9/2015 | Weber | G06F 3/044 382/125 |
| 2015/0347407 A1* | 12/2015 | Poiesz | G06F 17/30017 707/723 |
| 2015/0366518 A1* | 12/2015 | Sampson | A61B 5/7221 600/301 |
| 2016/0287172 A1* | 10/2016 | Morris | A61B 5/04085 |
| 2017/0045993 A1* | 2/2017 | Oh | G06F 3/0488 |

OTHER PUBLICATIONS

Majumder, S. "Wearable Sensors for Remote Health Monitoring" Sensors 2017, 17—www.mdpi.com/journal/sensors, pp. 1-45.*

European Search Report, Application No. EP 15 19 1613, 2 pages, Mar. 8, 2016.

* cited by examiner

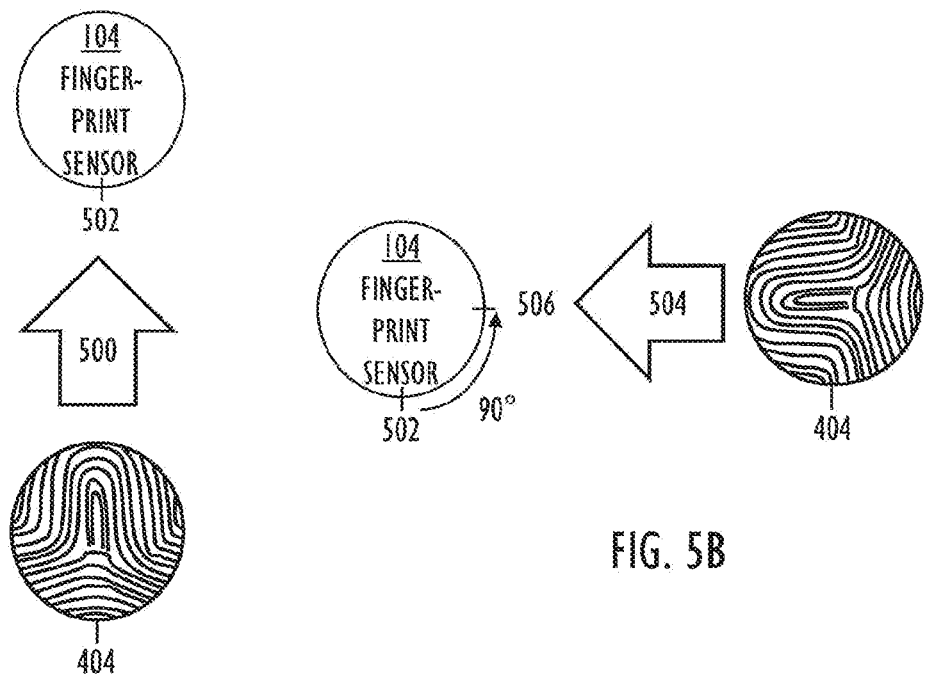
FIG. 5A
FIG. 5B
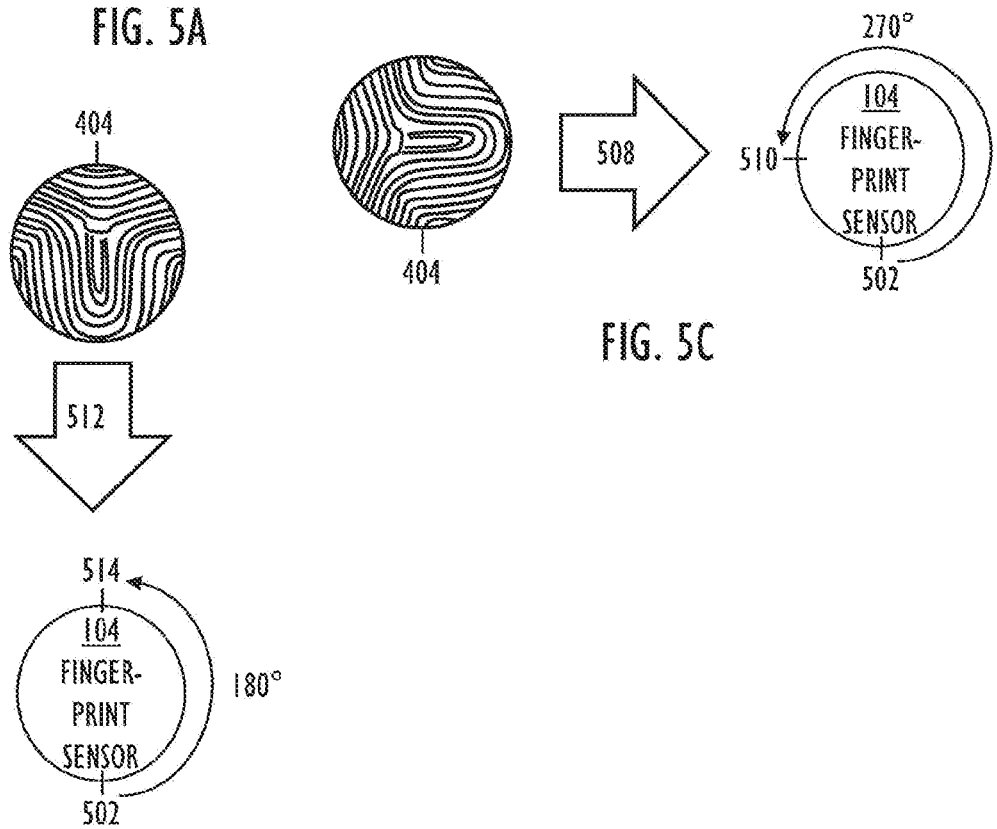
FIG. 5C
FIG. 5D

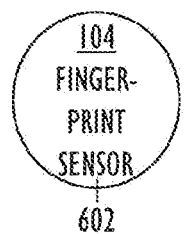
FIG. 6A
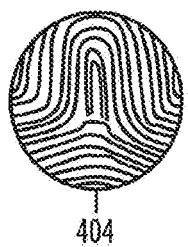
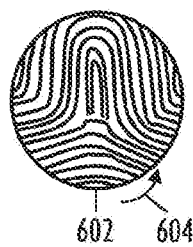 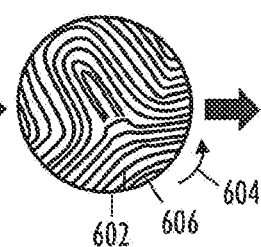 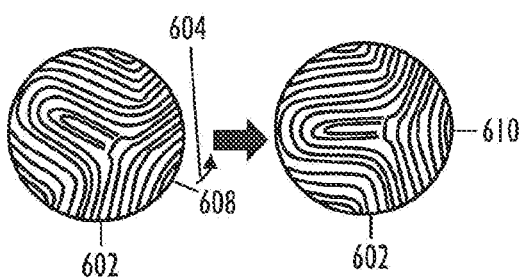
FIG. 6B     FIG. 6C     FIG. 6D     FIG. 6E
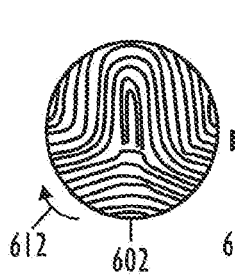 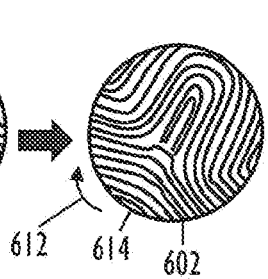 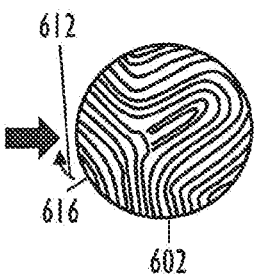 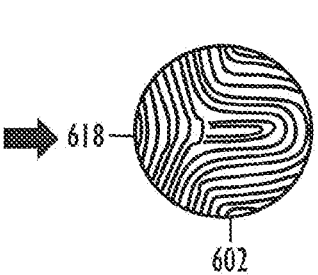
FIG. 6F     FIG. 6G     FIG. 6H     FIG. 6I

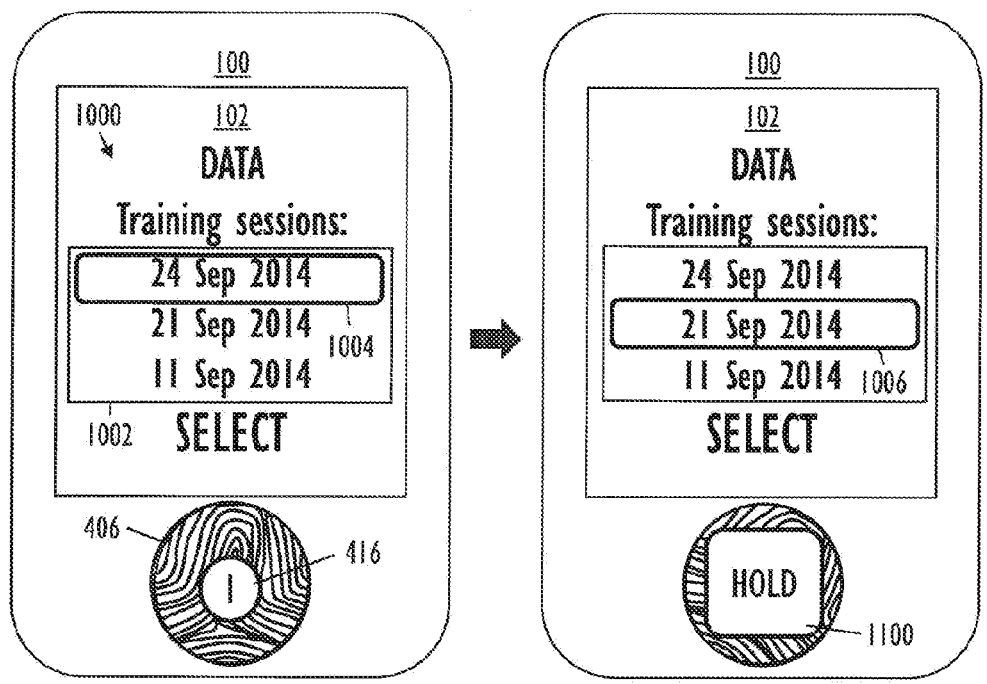
FIG. 11A
FIG. 11B
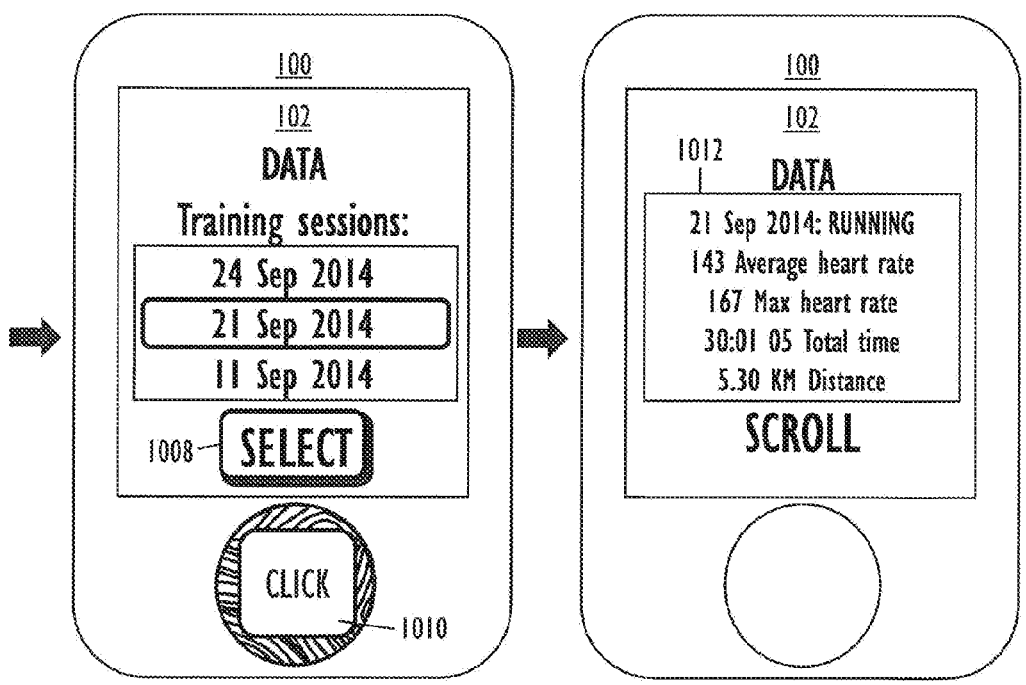
FIG. 11C
FIG. 11D

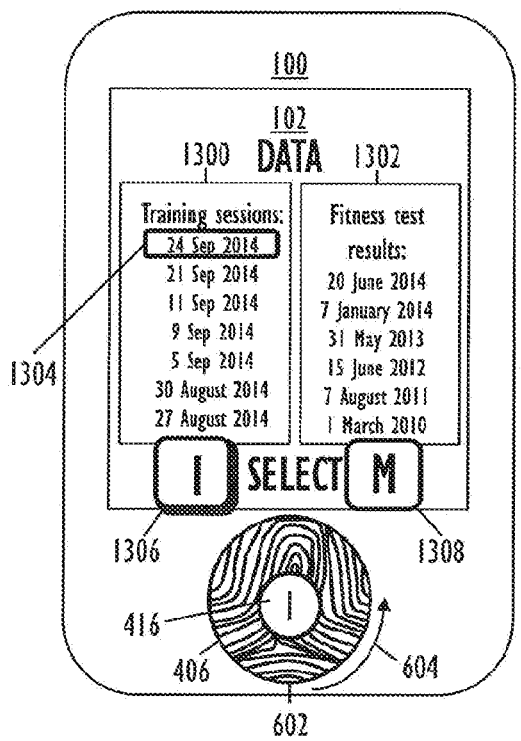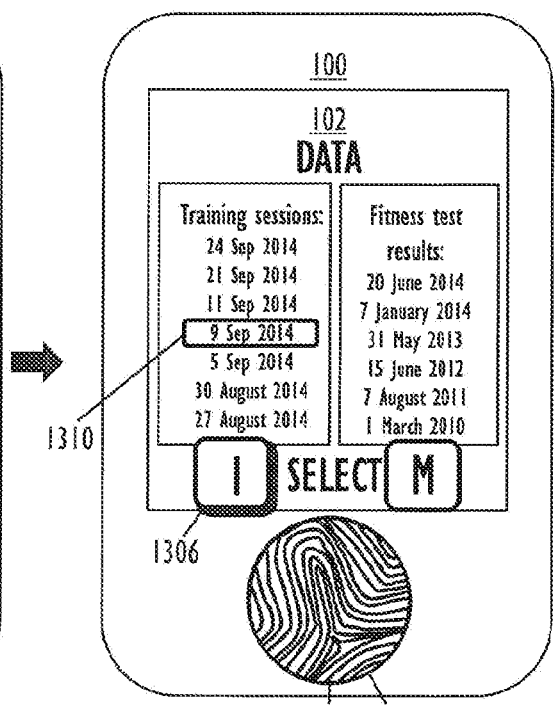
FIG. 13A  FIG. 13B
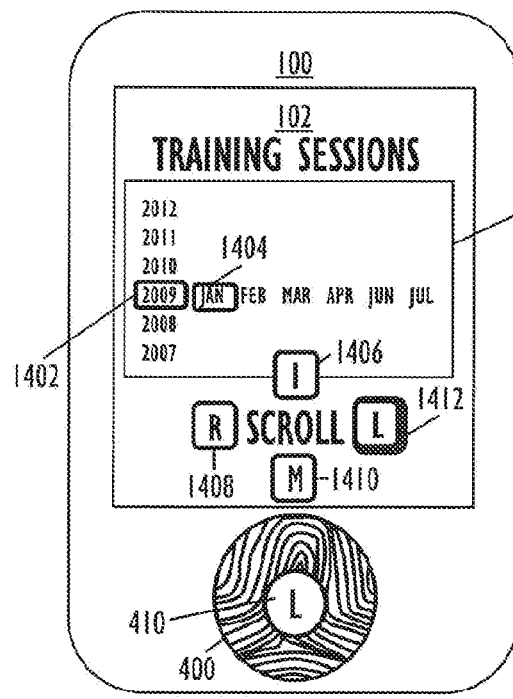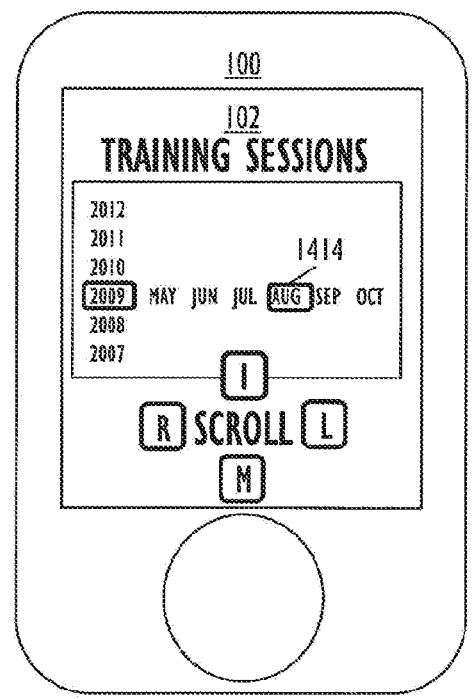
FIG. 14A  FIG. 14B

WRIST-WORN APPARATUS CONTROL WITH FINGERPRINT DATA

BACKGROUND

Field

The invention relates to an apparatus, a computer program and a method.

Description of the Related Art

Usability of user interfaces may be compromised for various reasons. A small display, for example, may cause complicated menu structures etc. Wrist-worn apparatuses capable of a physical activity-related measurement such as sports watches, utilize such small displays. Wrist-worn apparatuses typically utilize buttons or a touch display for user interaction, but their small size causes problems for usability (ease of use, learnability, precision)

SUMMARY

According to an aspect of the present invention, there is provided a wrist-worn apparatus comprising a physical activity-related measurement sensor interface, a fingerprint sensor, one or more processors, and one or more memories including computer program code, the one or more memories and the computer program code configured to, with the one or more processors, cause the apparatus at least to: receive fingerprint data from a user with the fingerprint sensor; identify the fingerprint data as matching with one finger of the user on the basis of a comparison between the fingerprint data and reference data of a plurality of fingers of the user stored in the memory; and select a function of a physical activity-related measurement on the basis of the identified finger.

According to another aspect of the present invention, there is provided a non-transitory computer-readable storage medium comprising a computer program comprising computer program code which, when loaded into an apparatus cause the apparatus to perform: receive fingerprint data from a user; identify the fingerprint data as matching with one finger of the user on the basis of a comparison between the fingerprint data and reference data of a plurality of fingers of the user; and select a function of a physical activity-related measurement on the basis of the identified finger.

According to another aspect of the present invention, there is provided a method comprising: receiving fingerprint data from a user; identifying the fingerprint data as matching with one finger of the user on the basis of a comparison between the fingerprint data and reference data of a plurality of fingers of the user; and selecting a function of a physical activity-related measurement on the basis of the identified finger.

BRIEF DESCRIPTION OF THE DRAWINGS

Example embodiments of the present invention are described below, by way of example only, with reference to the accompanying drawings, in which

FIGS. 5A, 5B, 5C, 5D, 6A, 6B, 6C, 6D, 6E, 6F, 6G, 6H and 6I illustrate various example embodiments of processing of fingerprint data;

FIGS. 7A, 7B, 7C, 7D, 8A, 8B, 9A, 9B, 10A, 10B, 10C, 10D, 11A, 11B, 11C, 11D, 12A, 12B, 12C, 12D, 13A, 13B, 14A and 14B illustrate various functions implemented in a user interface on the basis of the fingerprint data identification.

DETAILED DESCRIPTION

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments: the described fingerprint identification may be augmented with various other processing phases. Furthermore, words "comprising" and "including" should be understood as not limiting the described embodiments to consist of only those features that have been mentioned and such embodiments may contain also features/structures that have not been specifically mentioned.

Figure 1:
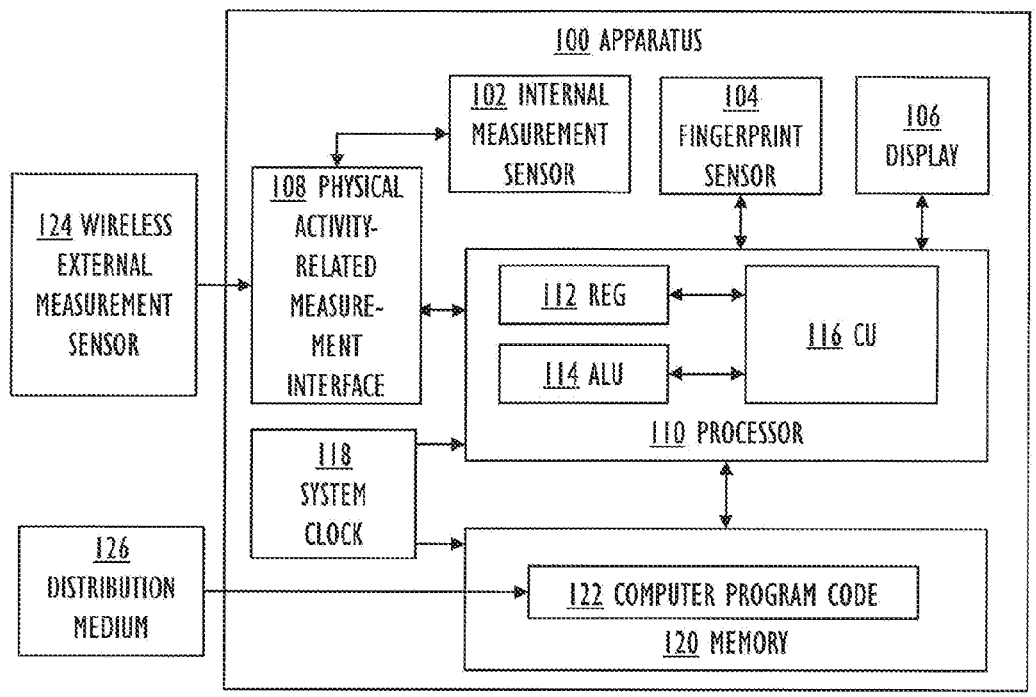
FIGS. 1, 2, 3 and 4 illustrate example embodiments of an apparatus.

FIG. 1 illustrates example embodiments of an apparatus 100. It should be noted that while FIG. 1 illustrates various example embodiments of the apparatus 100, it is only a simplified block diagram that only shows some structures and functional entities. The connections shown in FIG. 1 are logical connections; the actual physical connections may be different. It is apparent to a person skilled in the art that the described apparatus 100 may also comprise other functions and structures. It should be appreciated that details of some functions, structures, and the protocols used for communication are irrelevant to the actual invention. Therefore, they need not be discussed in more detail here.

The apparatus 100 comprises a physical activity-related measurement sensor interface 108, a fingerprint sensor 104, one or more processors 110, and one or more memories 120 including computer program code 122.

The physical activity-related measurement sensor interface 108 may be utilized to obtain measurement data obtained by monitoring a user of the apparatus 100.

In an example embodiment, the apparatus 100 may further comprise measurement sensors 102, 124. The sensors 102, 124 may produce the physical activity-related measurement data such as sports, exercise or activity related data. A non-exhaustive list of sensors 102, 124 includes heart rate sensors, motion sensors, location sensors, swimming sensors and bike sensors, as well as other sensors gathering information regarding the training. The heart rate sensors include, but are not limited to, a cardiovascular sensor (such as an electrocardiogram ECG sensor), and an optical heart rate sensor (heart rate, heart rate variability). Motion sensors may include accelerometers worn on chest, wrist, or ankle, for example. Location sensors may utilize GPS (Global Positioning System) or other satellite-based, or radio system-based system for locating the user and measuring various parameters (speed, distance, location, route) relating to the movement of the user. Swimming sensors may measure swimming specific parameters such as number of strokes or distance, for example. Bike sensors may be sensors attached to various parts of the bike for measuring speed, cadence, or power, for example. The gathered sensor information may be utilized to calculate further physical activity-related measurement data of the user such as a total energy consumption, an energy consumption speed, an activity level, a cumulated activity, for example.

As illustrated in FIG. 1, the sensors may be internal measurement sensors 102 (within the apparatus 100) and/or wireless external measurement sensors 124 (outside of the apparatus 100). The apparatus 100 may comprise a transceiver 108 for communicating with the wireless external measurement sensor(s) 124, or even just a receiver for receiving measurements from the wireless external measurement sensors 124. For the internal measurement sensors 102, the interface 108 may be a suitable hardware communication interface such as a wired interface or an appropriate communication bus.

The fingerprint sensor 104 receives fingerprint data from a user. Fingerprint data generated by the fingerprint sensor 104 refers to an image of the fingerprint pattern and/or to a description of such features (ridges forming patterns such as arches, loops and whorls or other fine details) that cause the uniqueness of the fingerprint. The description may be generated by applying a mathematical algorithm on the image in order to create a fingerprint template (=a representation of some distinguishing features of the fingerprint). Furthermore, for reasons of data security, the fingerprint template may be cryptographically hashed.

The fingerprint sensor 104 may utilize various technologies to generate the fingerprint data. These technologies include, but are not limited to optical and capacitance sensors. An optical fingerprint sensor 104 takes a picture of the fingerprint with a digital camera. A capacitance fingerprint sensor 104 detects differences in electrical conductivity caused by raised parts of the fingerprint and generates an image based on those differences.

The term 'processor' 110 refers to a device that is capable of processing data. Depending on the processing power needed, the apparatus 100 may comprise several processors 110 such as parallel processors or a multicore processor. When designing the implementation of the processor 110, a person skilled in the art will consider the requirements set for the size and power consumption of the apparatus 100, the necessary processing capacity, production costs, and production volumes, for example. The processor 110 and the memory 120 may be implemented by an electronic circuitry.

The term 'memory' 120 refers to a device that is capable of storing data run-time (=working memory) or permanently (=non-volatile memory). The working memory and the non-volatile memory may be implemented by a random-access memory (RAM), dynamic RAM (DRAM), static RAM (SRAM), a flash memory, a solid state disk (SSD), PROM (programmable read-only memory), a suitable semiconductor, or any other means of implementing an electrical computer memory.

In an example embodiment, a system clock 118 constantly generates a stream of electrical pulses, which cause the various transferring operations within the apparatus 100 to take place in an orderly manner and with specific timing.

In an example embodiment, the processor 110 may be implemented as a microprocessor implementing functions of a central processing unit (CPU) on an integrated circuit. The CPU is a logic machine executing a computer program code 122. The computer program code 122 may be coded as a computer program using a programming language, which may be a high-level programming language, such as C, or Java, or a low-level programming language, such as a machine language, or an assembler. The CPU may comprise a set of registers 112, an arithmetic logic unit (ALU) 114, and a control unit (CU) 116. The control unit 116 is controlled by a sequence of the computer program code 122 transferred to the CPU from the (working) memory 120. The control unit 116 may contain a number of microinstructions for basic operations. The implementation of the microinstructions may vary, depending on the CPU design. The microprocessor 110 may also have an operating system (a dedicated operating system of an embedded system, a real-time operating system, or even a general-purpose operating system), which may provide the computer program code 122 with system services.

A non-exhaustive list of implementation techniques for the processor 110 and the memory 120 includes, but is not limited to: logic components, standard integrated circuits, application-specific integrated circuits (ASIC), system-on-a-chip (SoC), application-specific standard products (ASSP), microprocessors, microcontrollers, digital signal processors, special-purpose computer chips, field-programmable gate arrays (FPGA), and other suitable electronics structures.

The computer program code 122 may be implemented by software and/or hardware. In an example embodiment, the software may be written by a suitable programming language, and the resulting executable code 122 may be stored on the memory 120 and run by the processor 110.

In an example embodiment, the functionality of the hardware may be designed by a suitable hardware description language (such as Verilog or VHDL), and transformed into a gate-level netlist (describing standard cells and the electrical connections between them), and after further phases the chip implementing the processor 110, memory 120 and the code 122 of the apparatus 100 may be fabricated with photo masks describing the circuitry.

In an example embodiment, the processor 110 and the memory 120 of the apparatus 100 are a part of a microcontroller.

In an example embodiment, the fingerprint sensor 104, the processor 110 and the memory 120 are separate entities, communicatively coupled together by an appropriate serial bus, for example. In general interfaces between the various elements may be implemented with suitable interface technologies, such as a message interface, a method interface, a sub-routine call interface, a block interface, an appropriate serial/parallel bus, or any hardware/software means enabling communication between various sub-units of the apparatus 100.

An example embodiment provides a computer-readable medium 126 for the apparatus 100 comprising a computer program comprising the computer program code 122. Said computer program code 122, when loaded into the apparatus 100 and executed in the apparatus 100, causes the apparatus 100 to receive fingerprint data from a user, identify the fingerprint data as matching with one finger of the user on the basis of a comparison between the fingerprint data and reference data of a plurality of fingers of the user, and select a function of a physical activity-related measurement on the basis of the identified finger. The computer program code 122 also performs the operations required to implement the described other example embodiments. In an example embodiment, the computer program code 122 may be in source code form, object code form, executable file, or in some intermediate form. The computer-readable medium 126 may comprise at least the following: any entity or device capable of carrying computer program code 122 to the apparatus 100, a record medium, a computer memory, a read-only memory, an electrical carrier signal, a telecommunications signal, and a software distribution medium. In some jurisdictions, depending on the legislation and the patent practice, the computer-readable medium 126 may not be the telecommunications signal. In an example embodiment, the computer-readable medium 126 may be a non-transitory computer readable storage medium.

In an example embodiment, the apparatus 100 comprises a display 106. The display 106 may be implemented with suitable technologies including, but not limited to at least the following: LCD (liquid crystal display), EL (electroluminescence), LED (light emitting diode), and OLED (organic light emitting diode).

A non-exhaustive list of apparatuses 100 includes but is not limited to: a wrist-worn sports watch, a bicycle computer, a mobile apparatus, or any other suitable apparatus for processing or displaying physical activity-related data such as sports, exercise or activity related data.

Figure 2:
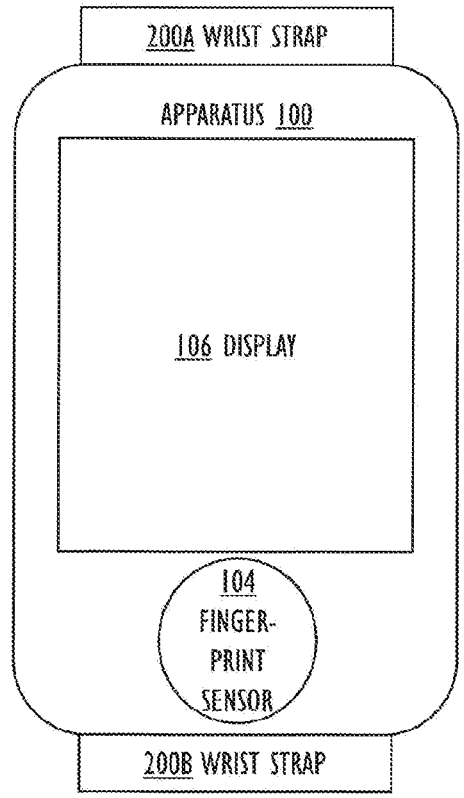

FIG. 2 illustrates an example embodiment of the apparatus 100: a wrist-worn measurement apparatus with the fingerprint sensor 104 and the display 106 facing outwards, and a wrist strap 200A, 200B for attaching the apparatus 100 to the wrist.

Figure 3:
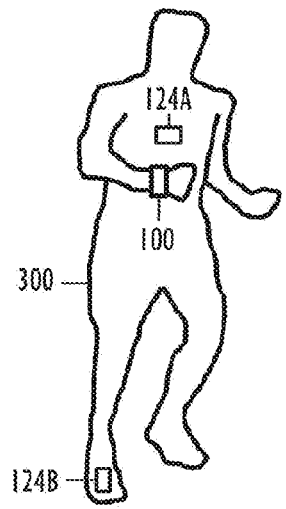

FIG. 3 illustrates an example embodiment where the apparatus 100 is implemented as a running computer, such as Polar RCX5. A user 300 is provided with the the wrist-worn apparatus 100. Furthermore, the user 300 may be provided with a heart rate transmitter 124A strapped around the chest, and possibly also with a shoe-mounted stride sensor 124B. The accessories 124A, 124B communicate wirelessly with the apparatus 100. Various accessories may be flexibly used as needed, i.e. all of them are not necessarily needed all the time, or by all users, or in all use cases.

However, in an example embodiment, the apparatus 100 may also be interpreted as a circuitry implementing the required functionality within some suitable equipment.

Figure 4:
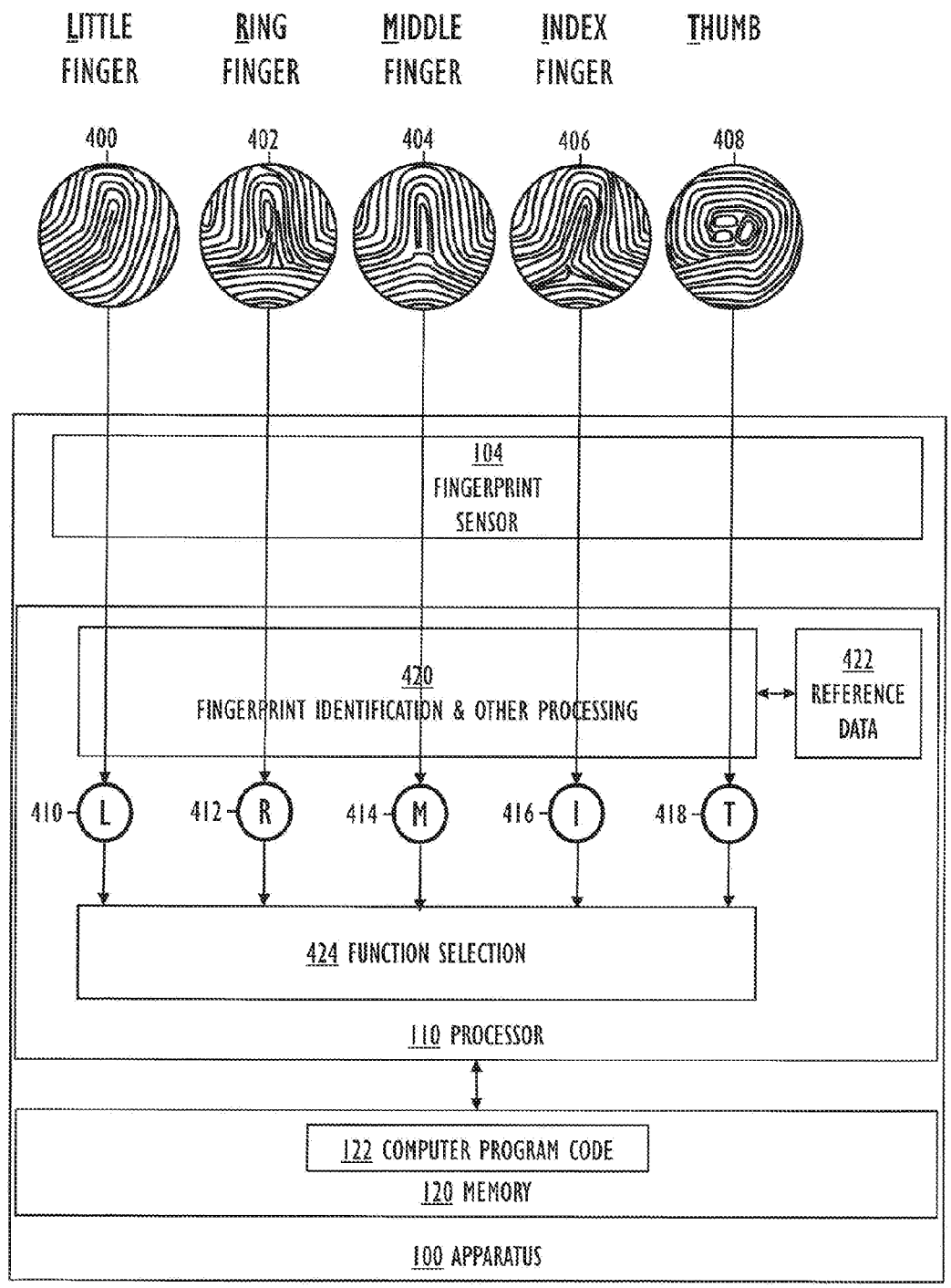

FIG. 4 illustrates further example embodiments of the apparatus 100.

The one or more memories 120 and the computer program code 122 of the apparatus 100 are configured to, with the one or more processors 110, cause the apparatus 100 at least to receive fingerprint data 400/402/404/406/408 from the user 300 with the fingerprint sensor 104, identify 420, 410/412/414/416/418 the fingerprint data 400/402/404/406/408 as matching with one finger of the user 300 on the basis of a comparison between the fingerprint data 400/402/404/406/408 and reference data 422 of a plurality of fingers of the user 300 stored in the memory 120, and select 424 a function of a physical activity-related measurement on the basis of the identified finger 410/412/414/416/418.

In the example embodiment, five fingers of the user 300, the little finger, ring finger, middle finger, index finger and thumb, are utilized, but any number of fingers from 1 to 10 may be utilized depending on the application and whether both hands may conveniently be used for user interaction with the apparatus 100 or whether only one hand may be utilized.

In an example embodiment, the fingerprint sensor 104 produces a hash of the fingerprint template 400/402/404/406/408, which is then compared with the stored reference 422 hashes of the fingers in order to identify the finger 410/412/414/416/418.

In an example embodiment, the one or more memories 120 and the computer program code 122 are further configured to, with the one or more processors 110, cause the apparatus 100 further to identify the fingerprint data as matching with one finger of the user on the basis of the comparison between the fingerprint data 400/402/404/406/408 and the reference data 422 of the plurality of fingers of the user 300 stored in the memory 120 such that the reference data 422 comprises a plurality of data elements, each data element comprising finger-specific reference data of a finger of the user 300 and a pointer to a single operation of the operation state in one of a collection of operations, a sequence of consecutive operations, and select the operation state of the apparatus 100 on the basis of the identified finger such that the single operation pointed to by the pointer in the data element of the identified finger is executed.

In an example embodiment, the pointer comprises a pointer to a memory location in the memory 120 storing an entry point to a function implementing the operation.

In an example embodiment, the pointer provides a shortcut to select the operation from the plurality of the operations.

In an example embodiment, the one or more memories 120 and the computer program code 122 are further configured to, with the one or more processors 110, cause the apparatus 100 further to set the apparatus 100 in a setting state on the basis of received user interface manipulation by the user 300, receive fingerprint learning data from the user 300 with the fingerprint sensor 104, and generate and store the reference data 422 on the basis of the received fingerprint learning data.

As was explained earlier, in an example embodiment the apparatus 100 further comprises the display 106. In a further example embodiment, the selected function comprises a user interface displayed on the display 106 comprising at least one of a control of an apparatus 100 internal sensor 102 measuring functioning of the body of the user 300, a control of an apparatus 100 external sensor 124 measuring functioning of the body of the user 300, a control of a heart rate measurement of the user 300, a control of an acceleration measurement related to a movement of the user 300, a control of a well-being measurement of the user 300, a control of a menu related to a sport exercised by the user 300, a control of a start of an exercise measuring function of the user 300, a control of a stop of the exercise measuring function of the user 300.

Besides control by the identified finger, further parameters may be detected by the fingerprint sensor 104.

As illustrated in FIGS. 5A, 5B, 5C and 5D, the one or more memories 120 and the computer program code 122 may further be configured to, with the one or more processors 110, cause the apparatus 100 further to identify an angular position of the finger in relation to a predetermined reference position 404 on the fingerprint sensor 104, and select 424 the function of the apparatus 100 on the basis of the identified finger and further on the basis of the identified angular position.

In FIG. 5A, the angular position of the fingerprint 404 is according to the reference position 502 as the finger is pressed 500 on the fingerprint sensor 104.

In FIG. 5B, the angular position 506 of the fingerprint 404 is turned 90 degrees from the reference position 502 as the finger is pressed 504 on the fingerprint sensor 104.

In FIG. 5C, the angular position 510 of the fingerprint 404 is turned 270 degrees from the reference position 502 as the finger is pressed 508 on the fingerprint sensor 104.

In FIG. 5D, the angular position 514 of the fingerprint 404 is turned 180 degrees from the reference position 502 as the finger is pressed 512 on the fingerprint sensor 104.

It is to be noted that these angular positions are just example embodiments as there may be more or less positions. For example positions of 0, 30, 60, 90 etc. degrees are still easy to use.

With the identified finger and its angular position, the number of different control gestures rises significantly: with five different fingers each having four possible angular positions there will be twenty different gestures.

As illustrated in FIGS. 6A, 6B, 6C, 6D, 6E, 6F, 6G, 6H and 6I, the one or more memories 120 and the computer program code 122 may further be configured to, with the one or more processors 110, cause the apparatus 100 further to identify a rotary movement of the finger on the fingerprint sensor 104, and select 424 the function of the apparatus 100 on the basis of the identified finger and further on the basis of the identified rotary movement.

In FIG. 6A, the finger is pressed 600 on the fingerprint sensor 104, whereupon the fingerprint 404 is detected in the reference position 602.

In an example embodiment, the one or more memories 120 and the computer program code 122 may further be configured to, with the one or more processors 110, cause the apparatus 100 further to identify a direction of the rotary movement either as a clockwise rotary movement or an anticlockwise rotary movement, and select 424 the function of the apparatus 100 on the basis of the identified finger, the identified rotary movement and further on the basis of the identified direction of the rotary movement.

In FIG. 6B, the fingerprint 404 is starting to turn 604 anticlockwise.

In FIG. 6C, the fingerprint 404 has performed a rotary movement 606 of 30 degrees, but it continues to turn 604.

In FIG. 6D, the fingerprint 404 has performed a rotary movement 608 of 60 degrees, but it continues to turn 604.

In FIG. 6E, has reached a rotary movement 610 of 90 degrees and stopped.

In FIG. 6F, the fingerprint 404 is starting to turn 612 clockwise.

In FIG. 6G, the fingerprint 404 has performed a rotary movement 614 of 30 degrees, but it continues to turn 612.

In FIG. 6H, the fingerprint 404 has performed a rotary movement 616 of 60 degrees, but it continues to turn 612.

In FIG. 6I, has reached a rotary movement 618 of 90 degrees and stopped.

With the identified finger and its rotary movement, the control possibilities are increased: the rotary movement may implement a sliding type continuous control or also a control sequence of steps following each other as a predetermined amount of rotary movement is detected.

Let us next study the already explained example embodiments and further example embodiments with reference to a simplified user interface illustrated in FIGS. 7A, 7B, 7C and 7D.

The apparatus 100 utilizes four functions.

Figure 7A:
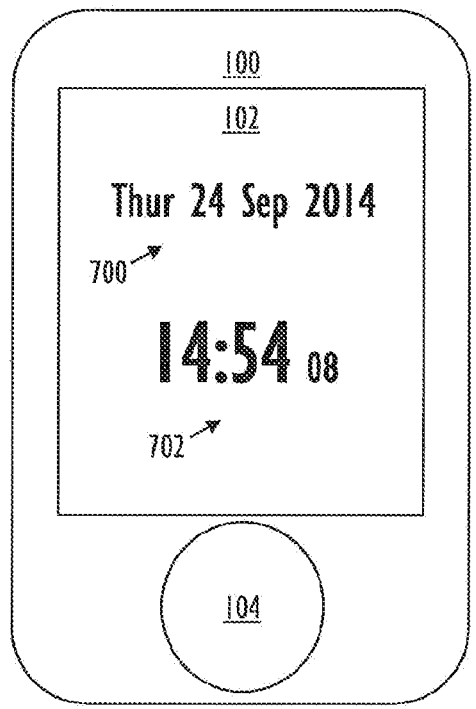

In FIG. 7A, the default function is shown. A watch function is displayed on the display 102: date 700 and time 702 are shown.

Figure 7B:
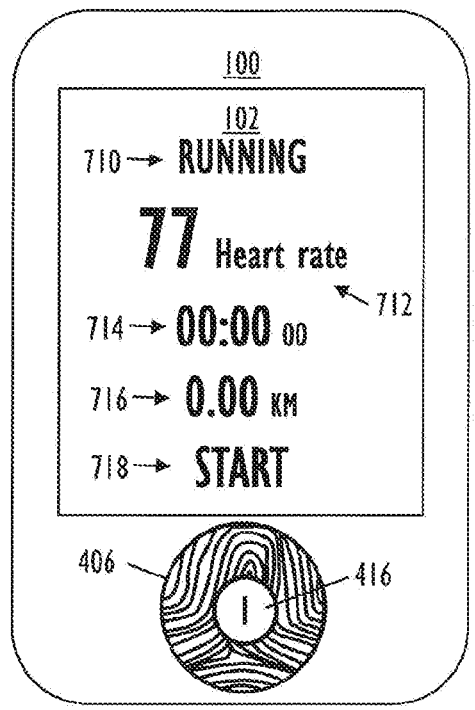

In FIG. 7B, the user has pressed his index finger on the fingerprint sensor 104, and the fingerprint 406 of the index finger has been identified 416. As a result of this function selection 424, 416, a sports measurement function is displayed on the display 102: running is the selected sport 710, the current heart rate 712 is 77 beat per minute, the exercise time 714 is still 00:00 and the distance is 0.00 km as the exercise has not yet been started, the next possible control (START) 718 is also indicated for the user 300.

Figure 7C:
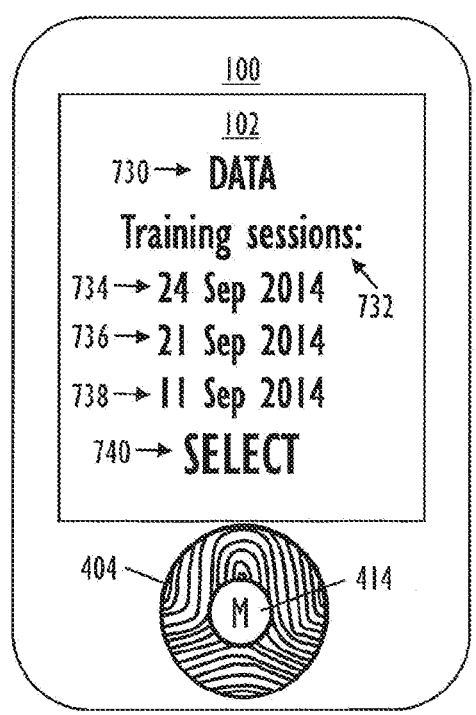

In FIG. 7C, the user has pressed his middle finger on the fingerprint sensor 104, and the fingerprint 404 of the index finger has been identified 414. As a result of this function selection 424, 414, a data function is displayed on the display 102: recorded training sessions 732 are displayed as a list with entries 734, 736, 738 on different days, and the next possible control (SELECT) 740 is also indicated for the user 300.

Figure 7D:
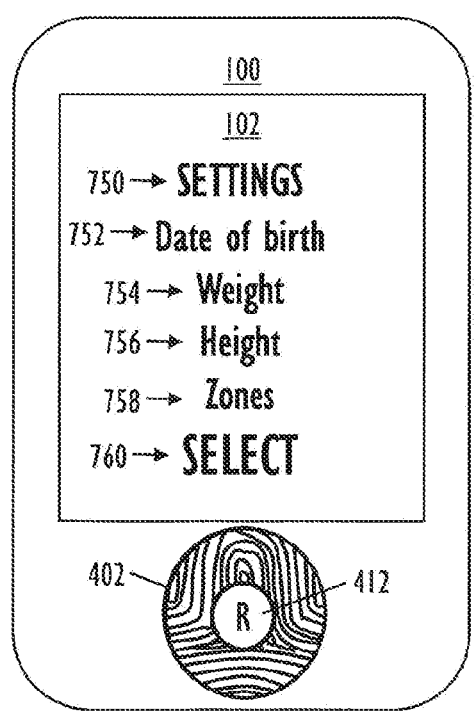

In FIG. 7D, the user has pressed his ring finger on the fingerprint sensor 104 and the fingerprint 402 of the index finger has been identified 412. As a result of this function selection 424, 412, a settings function is displayed on the display 102: various personal parameters (date of birth, weight, height, zones) 752, 754, 756, 758 are displayed, and the next possible control (SELECT) 760 is also indicated for the user 300.

Figure 8A:
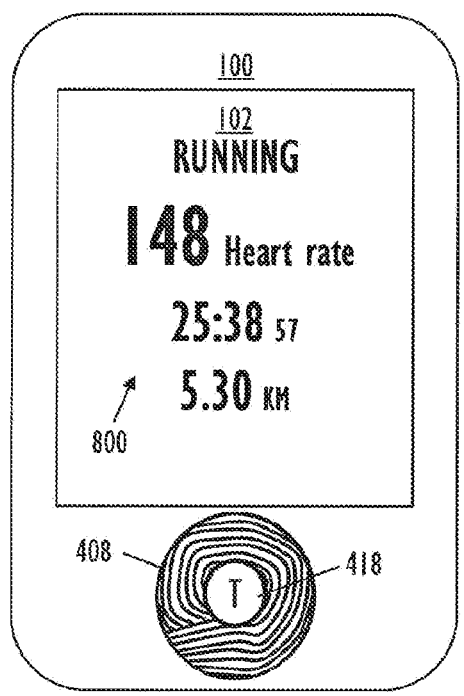
Figure 8B:
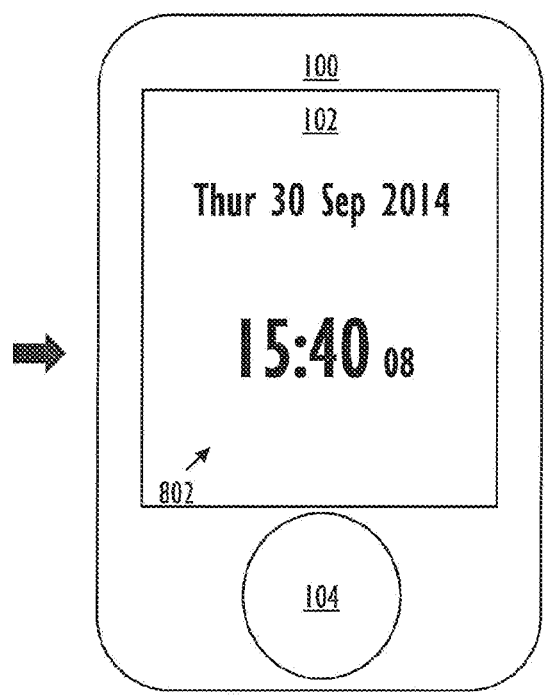

FIGS. 8A and 8B illustrate a further example embodiment. The one or more memories 120 and the computer program code 122 are further configured to, with the one or more processors 110, cause the apparatus 100 further to select 424, 418 a home button press as the function on the basis of an earlier assignment of a finger 408 of the user 300 to the home button press function, whereupon the apparatus 100 navigates to a predetermined page of the user interface displayed on the display 102. In FIG. 8A, the user 300 is in the middle of a running session, and the sport measurement function 800 is shown on the display 102. The user 300 presses his thumb on the fingerprint sensor 104, and, as this thumb pressing is interpreted 424, 418 as the home button press, the watch function 802 of FIG. 8B is consequently displayed.

In an example embodiment, the one or more memories 120 and the computer program code 122 are further configured to, with the one or more processors 110, cause the apparatus 100 further to wake up the apparatus 100 with the function of the user interface selected on the basis of the identified finger, whereupon the selected function is displayed on the display 100. This example embodiment is not illustrated in its own Figures, but we may refer to FIGS. 7B, 7C and 7D, for example: the apparatus 100 may be in a so-called sleep mode in order to save battery power, the display 102 may be turned off, for example. Now, the user 300 may wake up the apparatus with index, middle or ring finger, whereupon one of the functions of FIGS. 7B, 7C or 7D is displayed on the display 102 on the basis of the fingerprint identification 420 and function selection 424.

Figure 9A:
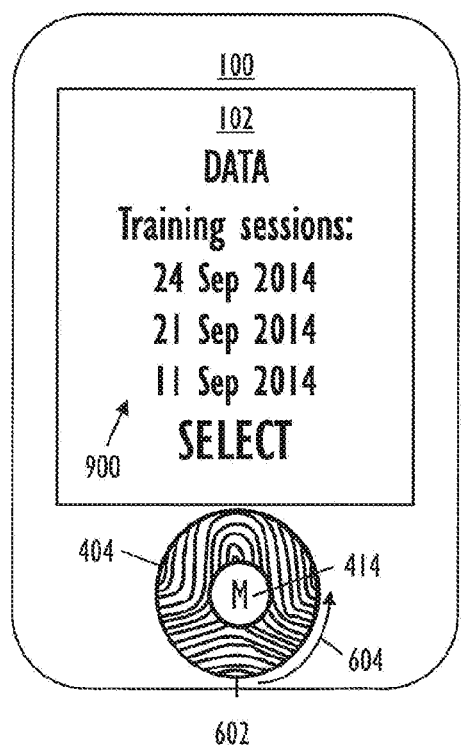
Figure 9B:
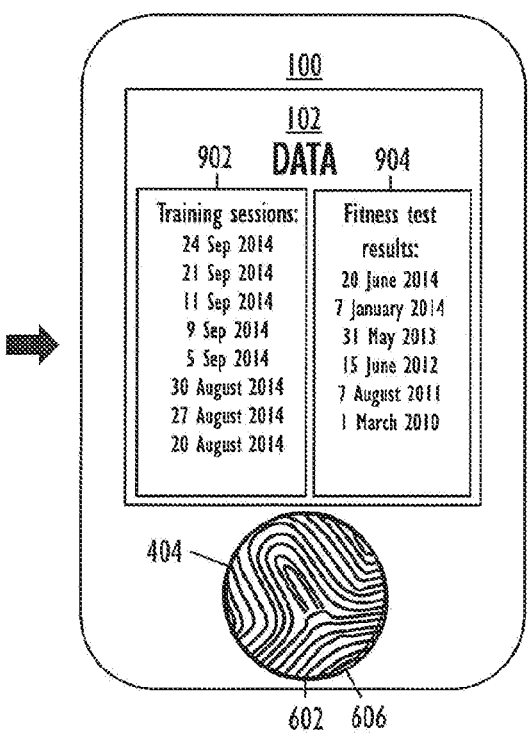

FIGS. 9A and 9B illustrate an example embodiment, wherein the one or more memories 120 and the computer program code 122 are further configured to, with the one or more processors 110, cause the apparatus 100 further to perform zoom control on the user interface displayed on the display 102 on the basis of the identified rotary movement. The principle of the rotary movement was already explained with reference to FIGS. 6A to 6I.

The user 300 is looking at the data function 900 and puts his middle finger on the fingerprint sensor 104 and starts to turn 604 the middle finger anticlockwise. The fingerprint 404 of the middle finger and the rotary movement 606 are identified 414, 420, whereupon the window is zoomed out and the view of FIG. 9B is shown: the training session window 902 is now smaller and another window 904 for fitness test results is shown on the side. With this example embodiment zoom control including continuous zooming in and zooming out may easily be implemented.

FIGS. 10A, 10B, 10C and 10D illustrate further example embodiments.

Figure 10A:
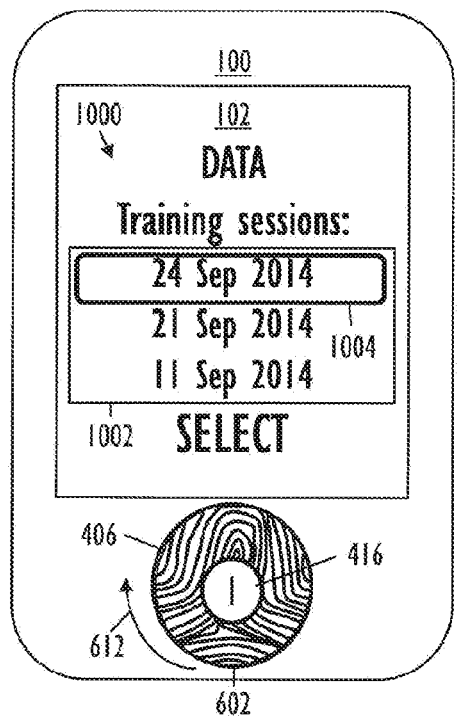
Figure 10B:
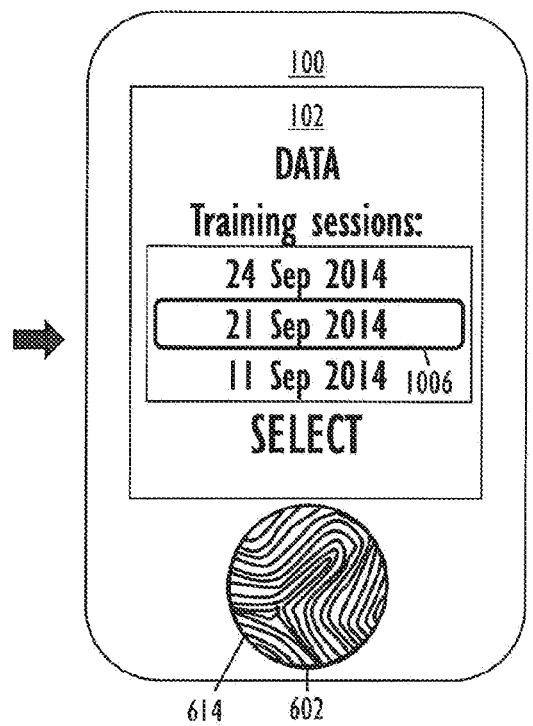

In an example embodiment, the one or more memories 120 and the computer program code 122 are further configured to, with the one or more processors 110, cause the apparatus 100 further to perform selection control on user interface elements of the user interface displayed on the display 102 on the basis of the identified rotary movement 614. In FIG. 10A, the user is watching at the data function 1000, where a scrollable window 1002 includes a list of the training sessions, and a selection pointer 1004 encircles one training session at a time. The user presses his index finger on the fingerprint sensor 104 and turns 612 the finger clockwise. As a result of this, as shown in FIG. 10B, the selection pointer 1006 moves to the next training session in the list.

Figure 10C:
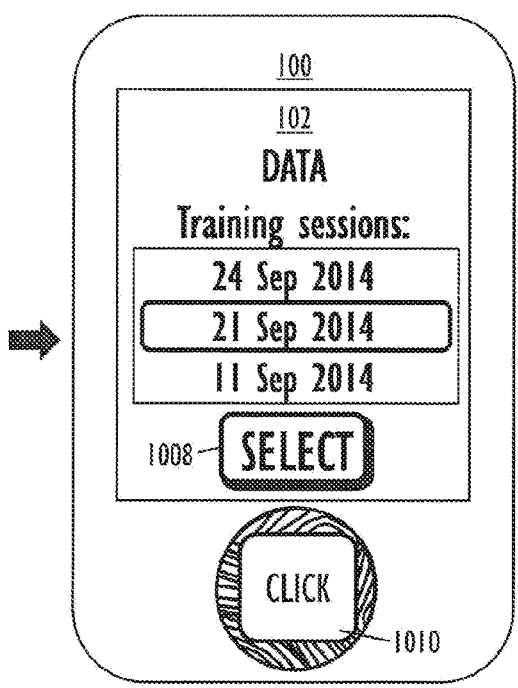
Figure 10D:
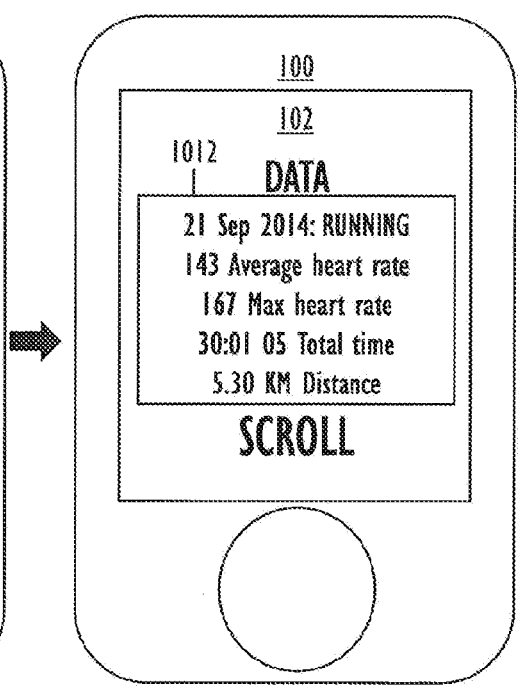

In an example embodiment, shown in FIG. 10C, the one or more memories 120 and the computer program code 122 are further configured to, with the one or more processors 110, cause the apparatus 100 further to detect clicking 1010 of the finger on the fingerprint sensor 104, and select 424, 1008 the function of the apparatus 100 on the basis of the identified finger and further on the basis of the detected clicking of the finger. FIG. 10D illustrates that the training session 1012 of 21 Sep. 2014 is displayed on the display 102 as a result of the function selection 424, 1008 with the clicking 1010 in FIG. 10C. The clicking 1010 may be implemented by integrating a pushbutton with the fingerprint sensor 104, for example. Another implementation possibility is to integrate a touch pad type of functionality with the fingerprint sensor 104, with resistive or capacitive technology used for touchscreens, for example.

FIGS. 11A, 11B, 11C and 11D illustrate the same operation sequence as FIGS. 10A, 10B, 10C and 10D, but implemented with a different example embodiment: instead of using the rotary movement, hold time is utilized for the additional control.

In an example embodiment, the one or more memories 120 and the computer program code 122 are further configured to, with the one or more processors 110, cause the apparatus 100 further to measure a hold time of the finger on the fingerprint sensor 104, and select the function of the apparatus 100 on the basis of the identified finger and further on the basis of the measured hold time.

In FIG. 11A, the user is watching at the data function 1000 with the scrollable window 1002 and the selection pointer 1004. The user presses his index finger on the fingerprint sensor 104 and as shown in FIG. 11B keeps his finger on the fingerprint sensor 104 which is recognized 420, 1100 and the hold time is measured. As a result of this, as shown in FIG. 11B, the selection pointer 1006 moves to the next training session in the list. FIG. 11D illustrates that the training session 1012 of 21 Sep. 2014 is displayed on the display 102 as a result of the function selection 424, 1008 with the clicking 1010 in FIG. 10C.

FIGS. 12A, 12B, 12C and 12D illustrate an example embodiment wherein the user interface is manipulated on the basis of the relative positions of different user interface elements.

In an example embodiment, the one or more memories 120 and the computer program code 122 are further configured to, with the one or more processors 110, cause the apparatus 100 further to select the function of the apparatus 100 on the basis of the identified finger such that the function is selected from among the selections displayed on the user interface such that different fingers relate to different relative positions on the user interface displayed on the display 102, wherein the different relative positions comprise at least one of left, middle, right, top, center, bottom, first, second, third, fourth, fifth, sixth, seventh, eighth, ninth, tenth, a first element on a list, a next element on the list, a last element on the list.

Figure 12A:
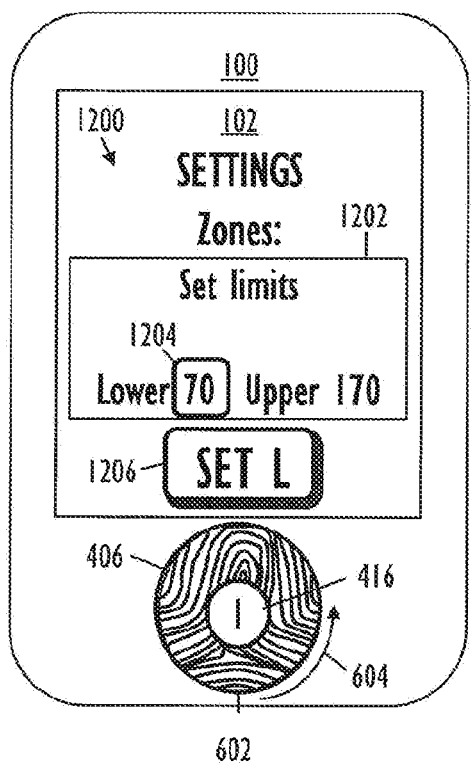

FIG. 12A illustrates an example embodiment, where zones 758 from settings 750 function illustrated in FIG. 7D has been opened for processing. The set limits function for the zones 1200 are shown in window 1202: the lower limit is currently 70 heartbeats per minute and the upper limit 170 heartbeats per minute. Now, the different relative positions are: the lower limit is on the left and the upper limit is on the right.

Figure 12B:
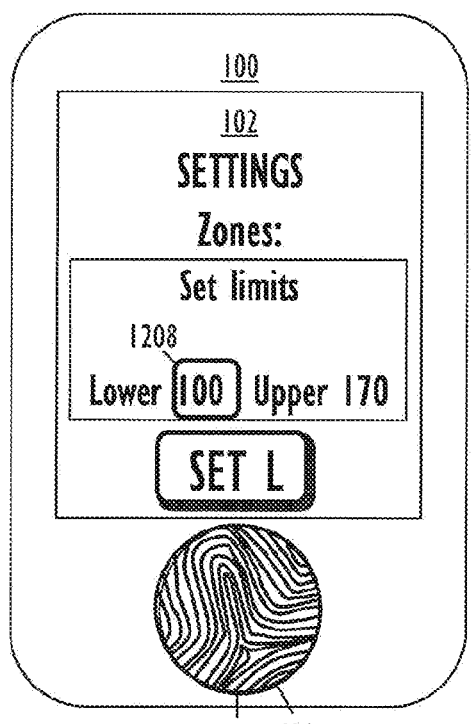

In FIGS. 12A and 12B the user 300 adjusts the lower limit by pressing his index finger on the fingerprint sensor 104, whereupon the fingerprint 406 of the index finger is identified 420, 416. As a result of this a set function 1206 is selected and a selection pointer 1204 is shown around the numerical value of the lower limit. Next, the user 300 starts to turn 604 his finger anticlockwise up to the angle 606. This causes that the lower limit is increased, number-by-number, up to 100 heartbeats per minute, circled with a selection pointer 1208.

Figure 12C:
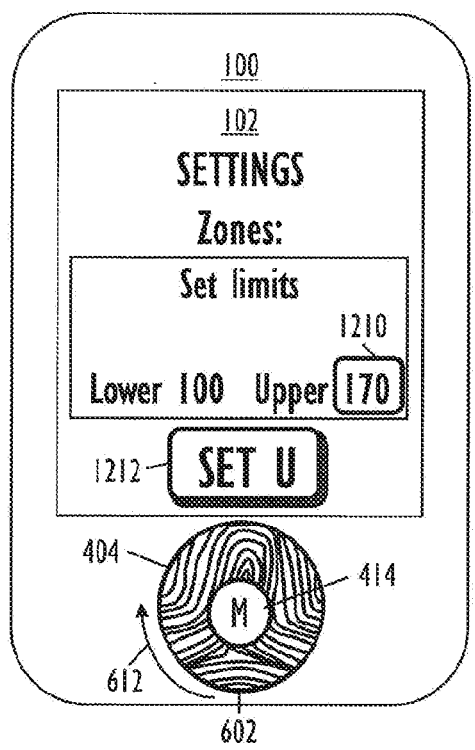
Figure 12D:
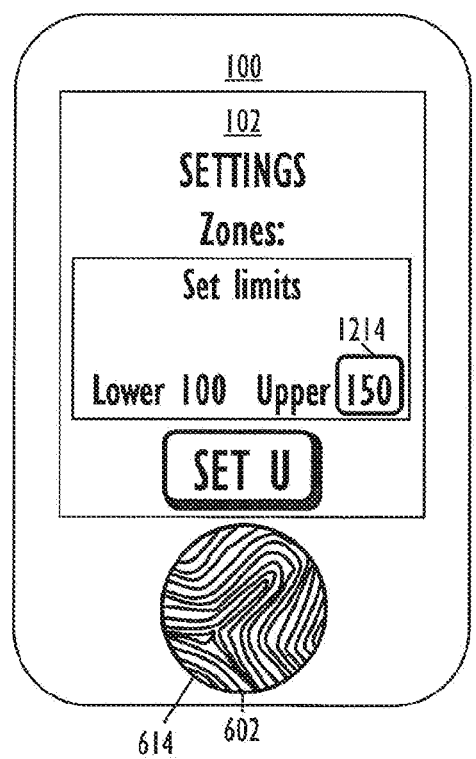

In FIGS. 12C and 12D the user 300 adjusts the upper limit by pressing his middle finger on the fingerprint sensor 104, whereupon the fingerprint 404 of the middle finger is identified 420, 414. As a result of this a set function 1212 is selected and a selection pointer 1210 is shown around the numerical value of the upper limit. Next, the user 300 starts to turn 612 his finger clockwise up to the angle 614. This causes that the upper limit is decreased, number-by-number, down to 150 heartbeats per minute, circled with a selection pointer 1214.

FIGS. 13A and 13B illustrate an example embodiment wherein the user interface is manipulated on the basis of the absolute positions of different user interface elements.

In an example embodiment, the one or more memories 120 and the computer program code 122 are further configured to, with the one or more processors 110, cause the apparatus 100 further to select the function of the apparatus 100 on the basis of the identified finger such that the function is selected from among selections displayed on the user interface such that different fingers relate to different absolute positions of the selections displayed on the display 102, wherein the different absolute positions comprise predetermined areas displayed on the display 102.

FIG. 13A illustrates an example embodiment, where data function from FIG. 9B is further manipulated: the training session window 1300 and the fitness test result window 1302 are side-by-side. The user 300 sees that the training session window 1300 may be manipulated with the index finger as a symbol I 1306 is shown beneath it. Similarly, the fitness test result window 1302 may be manipulated with the middle finger as a symbol M 1308 is shown beneath it. The user 300 chooses to manipulate the training session window 1300 by putting his index finger on the fingerprint sensor 104, whereupon the symbol I 1306 is shown as selected. The fingerprint 406 of the index finger is identified 420, 416. Next, the user 300 turns 604 his index finger to the angle 606, and, as a result of this, a selection pointer 1304 moves from "24 Sep. 2014" to a new position 1310 of "9 Sep. 2014".

FIGS. 14A and 14B illustrate an example embodiment wherein the user interface is scrolled with different fingers to different directions.

In an example embodiment, the one or more memories 120 and the computer program code 122 are further configured to, with the one or more processors 110, cause the apparatus 100 further to select the function of the apparatus 100 on the basis of the identified finger such that the function is selected from among scrolling directions of the user interface such that different fingers relate to the different scrolling directions of the user interface displayed on the display 102.

FIG. 14A now shows a wide view into the training session function: a scrollable window 1400 includes in the vertical line the years, and, for the selected year, on the horizontal line the months. Year 2009 is selected, as indicated by a first selection pointer 1402, and month January is selected, as indicated by a second selection pointer 1404. The scrolling directions are intuitively displayed on the display 102 with symbols up 1406, left 1408, down 1410, and right 1412. The user 300 presses his little finger on the fingerprint sensor 104, and the corresponding symbol, right, 1412 becomes highlighted as the fingerprint 400 of the little finger is identified 420, 410. FIG. 14B shows the end result of this function selection 424: a selection pointer 1414 is now shown over August, instead of January as in the beginning. FIGS. 14A and 14B do not show how the scrolling distance is determined, but this is easily implemented with the other described example embodiments: based on the hold the time, or the rotary movement, for example.

In an example embodiment, the one or more memories 120 and the computer program code 122 are further configured to, with the one or more processors 110, cause the apparatus 100 further to identify the fingerprint data and select the function of the physical activity-related measurement on the basis of the identified finger in a measurement mode of the apparatus 100. Such a function selection in the measurement mode has already been described with reference to FIGS. 7B and 8A, for example. Furthermore, the apparatus 100 is capable of distinguishing a consumer electronics mode of the apparatus 100, which is different from the measurement mode of the apparatus 100. The consumer electronics mode refers to an operation mode that is used in communications, entertainment or office equipment such as mobile phone or smartwatch. FIG. 7A, for example illustrates such a consumer electronics mode: a watch mode. Another example of such a consumer electronics mode is an interaction mode of a smartwatch with a mobile phone. The one or more memories 120 and the computer program code 122 are further configured to, with the one or more processors 110, cause the apparatus 100 further to select a function related to a consumer electronics functionality of the apparatus 100 on the basis of the identified finger such that a mapping of the identified finger and the selected function is different between the consumer electronics mode and the measurement mode. With this example embodiment, the user 300 may be provided with different user interface logics for the different modes (the consumer electronics mode and the measurement mode), which may improve the learnability of the user interface.

Figure 15:
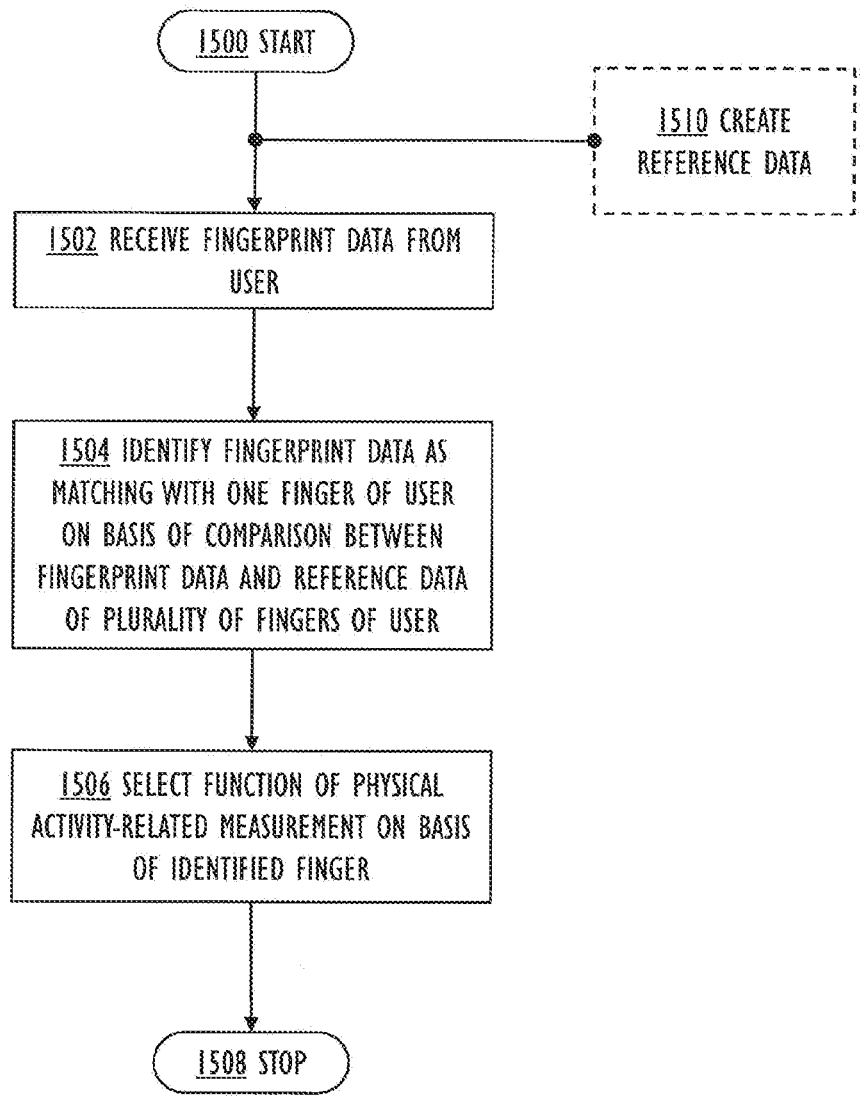
FIG. 15 is a flow-chart illustrating a method.

Next, let us study FIG. 15, which is a flow chart illustrating example embodiments of a method. The operations are not strictly in chronological order, and some of the operations may be performed simultaneously or in an order differing from the given ones. Other functions may also be executed between the operations or within the operations and other data exchanged between the operations. Some of the operations or part of the operations may also be left out or replaced by a corresponding operation or part of the operation. It should be noted that no special order of operations is required, except where necessary due to the logical requirements for the processing order. In an example embodiment, the method may be implemented by an electronic apparatus, by the described apparatus 100, for example.

The method starts in 1500.

In 1502, fingerprint data is received from a user.

In 1504, the fingerprint data is identified as matching with one finger of the user on the basis of a comparison between the fingerprint data and reference data of a plurality of fingers of the user.

In 1506, a function of a physical activity-related measurement is selected on the basis of the identified finger.

The method ends in 1508.

The already described example embodiments of the apparatus 100 may be utilized to enhance the method with various further example embodiments.

The operations and the supplementary operations may be repeated 1502-1504-1506 as required.

In an example embodiment of 1510, the reference data is created. This may be implemented such that the user 300 sets the apparatus 100 in a setting state on the basis of received user interface manipulation by the user. Next, the apparatus 100 receives fingerprint learning data from the user with the fingerprint sensor 104, and generates and stores the reference data on the basis of the received fingerprint learning data. The apparatus 100 may ask the user 300 to press each finger one-by-one on the fingerprint sensor 104, whereby each fingerprint is scanned and appropriate reference data 422 is generated.

It will be obvious to a person skilled in the art that, as technology advances, the inventive concept can be implemented in various ways. The invention and its embodiments are not limited to the example embodiments described above but may vary within the scope of the claims.

What is claimed is:

1. A wrist-worn apparatus comprising:
a physical activity-related measurement sensor interface;
a fingerprint sensor;
one or more processors;
a display; and
one or more non-transitory memories including computer program code, the computer program code configured to, with the one or more processors, cause the apparatus to perform operations comprising:
receiving fingerprint data from a user using the fingerprint sensor;
identifying the fingerprint data as matching with one finger of the user on the basis of a comparison between the fingerprint data and reference data of a plurality of fingers of the user stored in the one or more non-transitory memories;
selecting a function of a physical activity-related measurement on the basis of the identified finger;
detecting clicking of the finger on the fingerprint sensor;
selecting the function of the apparatus on the basis of the identified finger and further on the basis of the detected clicking of the finger, the selected function comprising a user interface displayed on the display comprising at least one of a control of an apparatus internal sensor measuring functioning of the body of the user, a control of an apparatus external sensor measuring functioning of the body of the user, a control of a heart rate measurement of the user, a control of an acceleration measurement related to a movement of the user, a control of a well-being measurement of the user, a control of a menu related to a sport exercised by the user, a control of a start of an exercise measuring function of the user, a control of a stop of the exercise measuring function of the user; and
selecting a home button press as the function on the basis of an earlier assignment of a finger of the user to the home button press function, whereupon the apparatus navigates to a predetermined page of the user interface displayed on the display.

2. The apparatus of claim 1, wherein the one or more memories and the computer program code are further configured to, with the one or more processors, cause the apparatus to perform operations comprising:

waking up the apparatus with the function of the user interface selected on the basis of the identified finger, whereupon the selected function is displayed on the display.

3. The apparatus of claim 1, wherein the one or more memories and the computer program code are further configured to, with the one or more processors, cause the apparatus to perform operations comprising:
measuring a hold time of the finger on the fingerprint sensor; and
selecting the function of the apparatus on the basis of the identified finger and further on the basis of the measured hold time.

4. The apparatus of claim 1, wherein the one or more memories and the computer program code are further configured to, with the one or more processors, cause the apparatus to perform operations comprising:
selecting the function of the apparatus on the basis of the identified finger such that the function is selected from among the selections displayed on the user interface such that different fingers relate to different relative positions on the user interface displayed on the display, wherein the different relative positions comprise at least one of left, middle, right, top, center, bottom, first, second, third, fourth, fifth, sixth, seventh, eighth, ninth, tenth, a first element on a list, a next element on the list, a last element on the list.

5. The apparatus of claim 1, wherein the one or more memories and the computer program code are further configured to, with the one or more processors, cause the apparatus to perform operations comprising:
selecting the function of the apparatus on the basis of the identified finger such that the function is selected from among selections displayed on the user interface such that different fingers relate to different absolute positions of the selections displayed on the display, wherein the different absolute positions comprise predetermined areas displayed on the display.

6. The apparatus of claim 1, wherein the one or more memories and the computer program code are further configured to, with the one or more processors, cause the apparatus to perform operations comprising:
selecting the function of the apparatus on the basis of the identified finger such that the function is selected from among scrolling directions of the user interface such that different fingers relate to the different scrolling directions of the user interface displayed on the display.

7. The apparatus of claim 1, wherein the one or more memories and the computer program code are further configured to, with the one or more processors, cause the apparatus to perform operations comprising:
setting the apparatus in a setting state on the basis of received user interface manipulation by the user;
receiving fingerprint learning data from the user with the fingerprint sensor; and
generating and storing the reference data on the basis of the received fingerprint learning data.

8. A wrist-worn apparatus comprising:
a physical activity-related measurement sensor interface;
a fingerprint sensor;
one or more processors; and
one or more non-transitory memories including computer program code, the computer program code configured to, with the one or more processors, cause the apparatus to perform operations comprising:
receiving fingerprint data from a user using the fingerprint sensor;
identifying the fingerprint data as matching with one finger of the user on the basis of a comparison between the fingerprint data and reference data of a plurality of fingers of the user stored in the one or more non-transitory memories;
selecting a function of a physical activity-related measurement on the basis of the identified finger;
identifying an angular position of the finger in relation to a predetermined reference position on the fingerprint sensor; and
selecting the function of the apparatus on the basis of the identified finger and further on the basis of the identified angular position.

9. A wrist-worn apparatus comprising:
a physical activity-related measurement sensor interface;
a fingerprint sensor;
one or more processors; and
one or more non-transitory memories including computer program code, the computer program code configured to, with the one or more processors, cause the apparatus to perform operations comprising:
receiving fingerprint data from a user using the fingerprint sensor;
identifying the fingerprint data as matching with one finger of the user on the basis of a comparison between the fingerprint data and reference data of a plurality of fingers of the user stored in the one or more non-transitory memories;
selecting a function of a physical activity-related measurement on the basis of the identified finger;
identifying a rotary movement of the finger on the fingerprint sensor; and
selecting the function of the apparatus on the basis of the identified finger and further on the basis of the identified rotary movement.

10. The apparatus of claim 9, wherein the one or more memories and the computer program code are further configured to, with the one or more processors, cause the apparatus to perform operations comprising:
identifying a direction of the rotary movement either as a clockwise rotary movement or an anticlockwise rotary movement; and
selecting the function of the apparatus on the basis of the identified finger, the identified rotary movement and further on the basis of the identified direction of the rotary movement.

11. The apparatus of claim 9, wherein the one or more memories and the computer program code are further configured to, with the one or more processors, cause the apparatus to perform operations comprising:
performing zoom control on the user interface displayed on the display on the basis of the identified rotary movement.

12. The apparatus of claim 9, wherein the one or more memories and the computer program code are further configured to, with the one or more processors, cause the apparatus to perform operations comprising:
performing selection control on user interface elements of the user interface displayed on the display on the basis of the identified rotary movement.

13. A wrist-worn apparatus comprising:
a physical activity-related measurement sensor interface;
a fingerprint sensor;
one or more processors; and
one or more non-transitory memories including computer program code, the computer program code configured to, with the one or more processors, cause the apparatus
to perform operations comprising:
receiving fingerprint data from a user using the fingerprint sensor;
identifying the fingerprint data as matching with one finger of the user on the basis of a comparison between the fingerprint data and reference data of a plurality of fingers of the user stored in the one or more non-transitory memories;
selecting a function of a physical activity-related measurement on the basis of the identified finger;
identifying the fingerprint data as matching with one finger of the user on the basis of the comparison between the fingerprint data and the reference data of the plurality of fingers of the user stored in the memory such that the reference data comprises a plurality of data elements, each data element comprising finger-specific reference data of a finger of the user and a pointer to a single operation of the operation state in one of a collection of operations, a sequence of consecutive operations; and
selecting the operation state of the apparatus on the basis of the identified finger such that the single operation pointed to by the pointer in the data element of the identified finger is executed.

14. The apparatus of claim 13, wherein the pointer comprises a pointer to a memory location in the memory storing an entry point to a function implementing the operation.

15. The apparatus of claim 13, wherein the pointer provides a shortcut to select the operation from the plurality of the operations.

16. A wrist-worn apparatus comprising:
a physical activity-related measurement sensor interface;
a fingerprint sensor;
one or more processors; and
one or more non-transitory memories including computer program code, the computer program code configured to, with the one or more processors, cause the apparatus to perform operations comprising:
receiving fingerprint data from a user using the fingerprint sensor;
identifying the fingerprint data as matching with one finger of the user on the basis of a comparison between the fingerprint data and reference data of a plurality of fingers of the user stored in the one or more non-transitory memories;
selecting a function of a physical activity-related measurement on the basis of the identified finger;
identifying the fingerprint data and select the function of the physical activity-related measurement on the basis of the identified finger in a measurement mode of the apparatus;
distinguishing a consumer electronics mode of the apparatus, which is different from the measurement mode of the apparatus; and
selecting a function related to a consumer electronics functionality of the apparatus on the basis of the identified finger such that a mapping of the identified finger and the selected function is different between the consumer electronics mode and the measurement mode.

17. A non-transitory computer-readable storage medium comprising a computer program comprising computer program code which, when executed by an apparatus, causes the apparatus to perform operations comprising:
receiving, using a fingerprint sensor, fingerprint data from a user;
identifying the fingerprint data as matching with one finger of the user on the basis of a comparison between the fingerprint data and reference data of a plurality of fingers of the user;
selecting a function of a physical activity-related measurement on the basis of the identified finger;
identifying an angular position of the finger in relation to a predetermined reference position on the fingerprint sensor; and
selecting the function of the apparatus on the basis of the identified finger and further on the basis of the identified angular position.

18. A method comprising:
receiving, using a fingerprint sensor, fingerprint data from a user;
identifying the fingerprint data as matching with one finger of the user on the basis of a comparison between the fingerprint data and reference data of a plurality of fingers of the user;
selecting a function of a physical activity-related measurement on the basis of the identified finger;
identifying an angular position of the finger in relation to a predetermined reference position on the fingerprint sensor; and
selecting the function of the physical activity-related measurement on the basis of the identified finger and further on the basis of the identified angular position.

19. A non-transitory computer-readable storage medium comprising a computer program comprising computer program code which, when executed by an apparatus, causes the apparatus to perform operations comprising:
receiving, using a fingerprint sensor, fingerprint data from a user;
identifying the fingerprint data as matching with one finger of the user on the basis of a comparison between the fingerprint data and reference data of a plurality of fingers of the user;
selecting a function of a physical activity-related measurement on the basis of the identified finger;
identifying a rotary movement of the finger on the fingerprint sensor; and
selecting the function of the apparatus on the basis of the identified finger and further on the basis of the identified rotary movement.

20. A non-transitory computer-readable storage medium comprising a computer program comprising computer program code which, when executed by an apparatus, causes the apparatus to perform operations comprising:
receiving, using a fingerprint sensor, fingerprint data from a user;
identifying the fingerprint data as matching with one finger of the user on the basis of a comparison between the fingerprint data and reference data of a plurality of fingers of the user;
selecting a function of a physical activity-related measurement on the basis of the identified finger;
detecting clicking of the finger on the fingerprint sensor;
selecting the function of the apparatus on the basis of the identified finger and further on the basis of the detected clicking of the finger, the selected function comprising a user interface displayed on a display comprising at least one of a control of an apparatus internal sensor measuring functioning of the body of the user, a control of an apparatus external sensor measuring functioning of the body of the user, a control of a heart rate measurement of the user, a control of an acceleration measurement related to a movement of the user, a control of a well-being measurement of the user, a control of a menu related to a sport exercised by the user, a control of a start of an exercise measuring function of the user, a control of a stop of the exercise measuring function of the user; and selecting a home button press as the function on the basis of an earlier assignment of a finger of the user to the home button press function, whereupon the apparatus navigates to a predetermined page of the user interface displayed on the display.

21. A non-transitory computer-readable storage medium comprising a computer program comprising computer program code which, when executed by an apparatus, causes the apparatus to perform operations comprising:

receiving, using a fingerprint sensor, fingerprint data from a user;

identifying the fingerprint data as matching with one finger of the user on the basis of a comparison between the fingerprint data and reference data of a plurality of fingers of the user;

selecting a function of a physical activity-related measurement on the basis of the identified finger;

identifying the fingerprint data as matching with one finger of the user on the basis of the comparison between the fingerprint data and the reference data of the plurality of fingers of the user stored in the memory such that the reference data comprises a plurality of data elements, each data element comprising finger-specific reference data of a finger of the user and a pointer to a single operation of the operation state in one of a collection of operations, a sequence of consecutive operations; and select the operation state of the apparatus on the basis of the identified finger such that the single operation pointed to by the pointer in the data element of the identified finger is executed.

22. A non-transitory computer-readable storage medium comprising a computer program comprising computer program code which, when executed by an apparatus, causes the apparatus to perform operations comprising:

receiving, using a fingerprint sensor, fingerprint data from a user;

identifying the fingerprint data as matching with one finger of the user on the basis of a comparison between the fingerprint data and reference data of a plurality of fingers of the user;

selecting a function of a physical activity-related measurement on the basis of the identified finger;

identifying the fingerprint data and selecting the function of the physical activity-related measurement on the basis of the identified finger in a measurement mode of the apparatus;

distinguishing a consumer electronics mode of the apparatus, which is different from the measurement mode of the apparatus; and selecting a function related to a consumer electronics functionality of the apparatus on the basis of the identified finger such that a mapping of the identified finger and the selected function is different between the consumer electronics mode and the measurement mode.

23. A method comprising:
receiving, using a fingerprint sensor, fingerprint data from a user;

identifying the fingerprint data as matching with one finger of the user on the basis of a comparison between the fingerprint data and reference data of a plurality of fingers of the user;

selecting a function of a physical activity-related measurement on the basis of the identified finger;

identifying a rotary movement of the finger on the fingerprint sensor; and selecting the function of the physical activity-related measurement on the basis of the identified finger and further on the basis of the identified rotary movement.

24. A method comprising:
receiving, using a fingerprint sensor, fingerprint data from a user;

identifying the fingerprint data as matching with one finger of the user on the basis of a comparison between the fingerprint data and reference data of a plurality of fingers of the user;

selecting a function of a physical activity-related measurement on the basis of the identified finger;

detecting clicking of the finger on the fingerprint sensor;

selecting the function of the physical activity-related measurement on the basis of the identified finger and further on the basis of the detected clicking of the finger, the selected function comprising a user interface displayed on a display comprising at least one of a control of an apparatus internal sensor measuring functioning of the body of the user, a control of an apparatus external sensor measuring functioning of the body of the user, a control of a heart rate measurement of the user, a control of an acceleration measurement related to a movement of the user, a control of a well-being measurement of the user, a control of a menu related to a sport exercised by the user, a control of a start of an exercise measuring function of the user, a control of a stop of the exercise measuring function of the user; and selecting a home button press as the function on the basis of an earlier assignment of a finger of the user to the home button press function, whereupon the apparatus navigates to a predetermined page of the user interface displayed on the display.

25. A method comprising:
receiving, using a fingerprint sensor, fingerprint data from a user;

identifying the fingerprint data as matching with one finger of the user on the basis of a comparison between the fingerprint data and reference data of a plurality of fingers of the user;

selecting a function of a physical activity-related measurement on the basis of the identified finger;

identifying the fingerprint data as matching with one finger of the user on the basis of the comparison between the fingerprint data and the reference data of the plurality of fingers of the user stored in the memory such that the reference data comprises a plurality of data elements, each data element comprising finger-specific reference data of a finger of the user and a pointer to a single operation of the operation state in one of a collection of operations, a sequence of consecutive operations; and selecting the operation state of an apparatus on the basis of the identified finger such that the single operation pointed to by the pointer in the data element of the identified finger is executed.

26. A method comprising:
receiving, using a fingerprint sensor, fingerprint data from a user;

identifying the fingerprint data as matching with one finger of the user on the basis of a comparison between the fingerprint data and reference data of a plurality of fingers of the user;

selecting a function of a physical activity-related measurement on the basis of the identified finger;

identifying the fingerprint data and selecting the function of the physical activity-related measurement on the basis of the identified finger in a measurement mode of an apparatus;

distinguishing a consumer electronics mode of the apparatus, which is different from the measurement mode of the apparatus; and selecting a function related to a consumer electronics functionality of the apparatus on the basis of the identified finger such that a mapping of the identified finger and the selected function is different between the consumer electronics mode and the measurement mode.

* * * * *

UNITED STATES PATENT AND TRADEMARK OFFICE
CERTIFICATE OF CORRECTION

PATENT NO.       : 9,721,141 B2
APPLICATION NO.  : 14/528632
DATED            : August 1, 2017
INVENTOR(S)      : Pertti Puolakanaho It is certified that error appears in the above-identified patent and that said Letters Patent is hereby corrected as shown below:

In the Specification

Column 10, Line 36:
Now reads: "a symbol 11306 is shown"
Should read: --a symbol 1306 is shown--

Signed and Sealed this
Third Day of April, 2018

Andrei Iancu
*Director of the United States Patent and Trademark Office*